United States Patent
Bonne

(10) Patent No.: US 7,494,326 B2
(45) Date of Patent: Feb. 24, 2009

(54) MICRO ION PUMP

(75) Inventor: Ulrich Bonne, Hopkins, MN (US)

(73) Assignee: Honeywell International Inc., Morristown, NJ (US)

( * ) Notice: Subject to any disclaimer, the term of this patent is extended or adjusted under 35 U.S.C. 154(b) by 657 days.

(21) Appl. No.: 10/765,517

(22) Filed: Jan. 27, 2004

(65) Prior Publication Data

US 2005/0141999 A1 Jun. 30, 2005

Related U.S. Application Data

(63) Continuation-in-part of application No. 10/749,863, filed on Dec. 31, 2003, and a continuation-in-part of application No. 10/750,483, filed on Dec. 31, 2003.

(51) Int. Cl.
*F04B 37/02* (2006.01)
*H02K 44/00* (2006.01)

(52) U.S. Cl. .................... 417/48; 417/50; 417/49

(58) Field of Classification Search .................. 417/48, 417/49, 50; 422/82.05
See application file for complete search history.

(56) References Cited

U.S. PATENT DOCUMENTS

| | | | |
|---|---|---|---|
| 906,468 A | 12/1908 | Steynis | |
| 1,157,859 A | 10/1915 | Freet | |
| 1,454,219 A | 5/1923 | Goedicke | |
| 1,505,669 A | 8/1924 | Quain | |
| 3,146,616 A | 9/1964 | Loyd | |
| 3,554,669 A * | 1/1971 | Reader | 417/48 |
| 3,557,532 A | 1/1971 | Broerman | |
| 3,730,874 A | 5/1973 | Trub | |
| 3,783,356 A | 1/1974 | Lide, III et al. | |
| 3,833,492 A | 9/1974 | Bollyky | |
| 3,921,002 A | 11/1975 | Williams | |

(Continued)

FOREIGN PATENT DOCUMENTS

DE 2 934 566 A1 3/1981

(Continued)

OTHER PUBLICATIONS

Amano, "Infrared spectroscopic detection of ions and free radicals in discharge plasmas," pp. 72-82, SPIE Proceedings, vol. 1858, 1993.

(Continued)

*Primary Examiner*—Devon Kramer
*Assistant Examiner*—Peter J Bertheaud
(74) *Attorney, Agent, or Firm*—Kris T. Fredrick

(57) ABSTRACT

An ion pump having conductive electrodes on both sides of an insulator which may form a number of channels. These electrodes may provide electrical discharges which have a corona or cold cathode emission for ionization. The electrodes and the insulator may be layers having openings that form the channels. The openings in one electrode layer may have a sharp-like configuration and the openings in the other electrode layer may have a non-sharp-like configuration. Ions may be predominately in-situ generated proximate to the sharp-like openings and have the polarity of these openings. These ions may induce a fluid flow through the channels of neutral molecules as a result of a force and viscous drag of the ions. The sharp-like openings may have nanotube whiskers or a thin film structure for facilitating an electrical discharge.

3 Claims, 12 Drawing Sheets

U.S. PATENT DOCUMENTS

| | | |
|---|---|---|
| 3,967,131 A | 6/1976 | Slipiec et al. |
| 3,979,193 A | 9/1976 | Sikich |
| 4,025,441 A | 5/1977 | Tabata et al. |
| 4,043,196 A | 8/1977 | Trageser |
| 4,048,668 A | 9/1977 | von Bargen |
| 4,049,552 A | 9/1977 | Arff |
| 4,051,045 A | 9/1977 | Yamamoto et al. |
| 4,079,260 A | 3/1978 | Dmietriev et al. |
| 4,101,783 A | 7/1978 | Hutter |
| 4,123,664 A | 10/1978 | Yamamura et al. |
| 4,128,768 A | 12/1978 | Yamamoto et al. |
| 4,159,971 A | 7/1979 | Gneupel |
| 4,216,096 A | 8/1980 | Pare et al. |
| 4,228,815 A | 10/1980 | Juffa et al. |
| 4,234,800 A | 11/1980 | Kenly |
| 4,383,976 A | 5/1983 | Notaro |
| 4,411,756 A | 10/1983 | Bennett et al. |
| 4,417,966 A | 11/1983 | Krauss et al. |
| 4,461,744 A | 7/1984 | Erni et al. |
| 4,478,076 A | 10/1984 | Bohrer |
| 4,483,200 A | 11/1984 | Togawa et al. |
| 4,504,446 A | 3/1985 | Kunicki et al. |
| 4,507,974 A | 4/1985 | Yelderman |
| 4,576,050 A | 3/1986 | Lambert |
| 4,614,573 A | 9/1986 | Masuda |
| 4,640,782 A | 2/1987 | Burleson |
| 4,650,573 A | 3/1987 | Nathanson |
| 4,656,010 A | 4/1987 | Leitzke |
| 4,690,803 A | 9/1987 | Hirth |
| 4,696,800 A | 9/1987 | Sasaki et al. |
| 4,725,412 A | 2/1988 | Ito |
| 4,735,082 A | 4/1988 | Kolloff |
| 4,759,210 A | 7/1988 | Wohltjen |
| 4,764,349 A | 8/1988 | Arff et al. |
| 4,877,588 A | 10/1989 | Ditzler et al. |
| 4,886,645 A | 12/1989 | Fischer et al. |
| 4,909,078 A | 3/1990 | Sittler et al. |
| 4,944,035 A | 7/1990 | Aagardl et al. |
| 4,960,569 A | 10/1990 | Fovell et al. |
| 4,969,850 A | 11/1990 | Wales |
| 4,981,656 A | 1/1991 | Leitzke |
| 5,004,587 A | 4/1991 | Tacchi |
| 5,008,087 A | 4/1991 | Batchelor |
| 5,031,126 A | 7/1991 | McCulloch et al. |
| 5,034,198 A | 7/1991 | Kaiga et al. |
| 5,044,766 A | 9/1991 | Stuart |
| 5,056,047 A | 10/1991 | Sondergeld |
| 5,093,087 A | 3/1992 | Freeman |
| 5,106,589 A | 4/1992 | Conrad |
| 5,124,132 A | 6/1992 | Francis, Jr. et al. |
| 5,145,653 A | 9/1992 | Fischer et al. |
| 5,146,414 A | 9/1992 | McKown et al. |
| 5,243,858 A | 9/1993 | Erskine et al. |
| 5,263,380 A | 11/1993 | Sultan et al. |
| 5,268,151 A | 12/1993 | Reed et al. |
| 5,268,302 A | 12/1993 | Rounbehler et al. |
| 5,379,630 A | 1/1995 | Lacey |
| 5,411,713 A | 5/1995 | Iwanaga |
| 5,463,899 A | 11/1995 | Zemel et al. |
| 5,469,013 A | 11/1995 | Kang |
| 5,533,412 A | 7/1996 | Jerman et al. |
| 5,570,179 A | 10/1996 | Weckstrom |
| 5,587,520 A | 12/1996 | Rhodes |
| 5,591,896 A | 1/1997 | Lin |
| 5,665,604 A | 9/1997 | Monagle et al. |
| 5,836,750 A | 11/1998 | Cabuz |
| 5,922,974 A | 7/1999 | Davison et al. |
| 5,968,377 A | 10/1999 | Yuasa et al. |
| 6,016,027 A | 1/2000 | DeTemple et al. |
| 6,031,711 A * | 2/2000 | Tennent et al. ............... 361/303 |
| 6,106,236 A * | 8/2000 | Henoch et al. ................ 417/50 |
| 6,106,245 A | 8/2000 | Cabuz |
| 6,139,384 A | 10/2000 | DeTemple et al. |
| 6,178,811 B1 | 1/2001 | Bonne et al. |
| 6,179,586 B1 | 1/2001 | Herb et al. |
| 6,184,607 B1 | 2/2001 | Cabuz et al. |
| 6,194,833 B1 | 2/2001 | DeTemple et al. |
| 6,308,553 B1 | 10/2001 | Bonne et al. |
| 6,313,638 B1 | 11/2001 | Sun et al. |
| 6,393,894 B1 | 5/2002 | Bonne et al. |
| 6,457,347 B1 | 10/2002 | Koo et al. |
| 6,494,617 B1 | 12/2002 | Stokes et al. |
| 6,583,407 B1 * | 6/2003 | Fischer et al. ............... 250/288 |

FOREIGN PATENT DOCUMENTS

| | | |
|---|---|---|
| DE | 32 34 146 A1 | 3/1984 |
| DE | 42 22 458 A1 | 1/1994 |
| DE | 42 43 573 A1 | 6/1994 |
| DE | 296 07 315 U1 | 9/1996 |
| DE | 196 19 133 A1 | 11/1997 |
| EP | 0 232 719 A1 | 1/1987 |
| EP | 0 348 245 A2 | 12/1989 |
| EP | 0 364 982 A2 | 4/1990 |
| EP | 0 419 873 A2 | 8/1990 |
| EP | 0 468 793 A2 | 1/1992 |
| EP | 0 702 212 A2 | 3/1996 |
| EP | 0 773 432 A2 | 5/1997 |
| GB | 2 287 792 A | 9/1995 |
| JP | 56-153256 | 11/1981 |
| JP | 57-131029 | 8/1982 |
| JP | 57-206830 | 12/1982 |
| WO | WO 92/06369 | 4/1992 |
| WO | WO 94/20825 | 9/1994 |
| WO | WO 98/22793 | 5/1998 |

OTHER PUBLICATIONS

Atalla et al., "Radiation Effects with the AC Heated Strip Technique for the Measurement of Thermal Properties of Liquids", *High Temperatures—High Pressures*, vol. 17, pp. 447-452, 1985.

Atalla et al. "Measurement of Thermal Properties of Liquids with an AC Heated-Wire Technique", *International Journal of Thermophysics*, vol. 2, No. 2, 1981.

Bonne et al., "Industrial Wireless PHASED Sensor Phase 1. Feasibility Demonstration," Progress Report for 4th Quarter of 2002, pp. 1-17, Jan. 31, 2002.

Bonne, et al., "Actuation-based microsensors," Smart Materials and Structures, 10, pp. 1185-1195, 2001.

Bonne, et al., "PHASED, a Faster, Smarter and More Affordable Gas Analysis Device—Update," International Forum on Process Analytical Chemistry (IFPAC) Scottsdale, AZ, Jan. 21-24, 2003.

Bonne, et al., "PHASED: a Faster, Smarter and More Affordable Gas Analysis Device," 16th International Forum on Process Analytical Chemistry, San Diego, CA., Jan. 22-25, 2002, pp. 1-17.

Bonne,U., et al., "New Gas Composition and Trace Contaminant Sensors," GTI Natural Gas Technologies Conference, Orland, FL, Sep. 30-Oct. 2, 2002, pp. 1-12.

Bottner et al., "Euler/Lagrange Calculations of Particle Motion in Turbulent Flow Coupled with an Electric Field," ECCOMAS Computational Fluid Dynamics Conference 2001, Swansea, Wales, UK, pp. 1-20, Sep. 4-7, 2001.

Cabuz, C. et al., "Mesoscopic Sampler Based on 3-DF Arrays of Electrostatically Actuated Diaphragms," Proc. 10th Conf. S.S. S&A. Transducers '99 Jun. 7-12, 1999, Sendai, Japan.

Cabuz, C., et al., "The Dual Diaphragm Pump," IEEE, pp. 519-522, 2001.

Chattock, "On the Velocity and Mass of the Ions in the Electric Wind in Air," Philosophical Magazine and Journal of Science, pp. 401-420, Nov. 1899.

Fuggerth, Endre, "Zone Gas Chromatography," Analytical Chemistry, 61, No. 14, pp. 1478-1485, (1989).

Hauksbee, "Phyfico-Mechanical Experiments on Various Subjects," London, pp. 53-64, 1709.

Herring, "Microdischarge-Based Detection Systems," DARPA Workshop on Micro Gas Analyzers, Monterey, CA., 8 pages, Dec. 2002.

Honeywell Electronic Materials Interconnect Solutions, Thin Films—Dielectrics, Comparison of Solution and film Properties, Advanced Products for IC Fabrication, 1 page.

http://www.advanced-polymers.com/star_center/techincal_papers/reduction_in_effective_dielectric_constant.pdf, 1 page.

http://www.chrompack.com/cgi/applicsview?ap=A00607 &Go=GO, NexTrieve document view, 2 pages, printed Dec. 26, 2002.

http://www.dicomps.com/uhv/iodipwer.htm, Ion Pump Power Source, 2 pages, printed Jun. 12, 2004.

http://www.zoex.com/html/technote_kt030505-1.html, Zoex Corporation, "A New Window on the Che," 5 pages, printed Mar. 15, 2004.

http://wwww.emd.horiba.com/engmease/mexa720nox, HORIBA Engine Measurement Division: MEXA-720Nox—Non-Sampling type Nox A . . . , 3 pages printed Oct. 1, 2004.

http://www.google.com/search?q=cache:oTL_3mJ7qQ4J:www.gas.lactec.org.br/down, "Miniaturized Ion Mobility Spectrometer," Mini 4seiter, G.A.S. Gesellschaft fur analytische Sensorsysteme mbH, 6 pages, printed Oct. 6, 2004.

International Search Report, PCT/US00/19924, mailed Mar. 5, 2001, 7 pages.

Kenndler, Ernst, "Gas Chromatography," Institute for Analytical Chemistry, University of Vienna, pp. 1-34, Sep. 9, 1999.

Kindlund et al., "Quartz Crystal Gas Monitor With Gas Concentrating Stage," Sensors and Actuators, 6 (1984) pp. 1-17.

Lee, et al., "The Study of Atmospheric Pressure Plasma by Large Area Capillary Electrode and It's Application," E-MRS Spring Meeting 2002, Jun. 18-21, 2002, pp. 440-746. (Abstract).

Mahadeva Sinha, "Development of a Miniature Lightweight Ion Pump," Miniature Pumps Workshop 2002, http://cot.marine.usf.edu/hems/workshop/Workshop%203rd/Abstracts%203rd/3rdpumpstalks.htm., (Abstract provided).

Park, et al., "Microdischarge Arrays: A New Family of Photonic Devices (Revised)," IEEE Journal on Selected Topics in Quantum Electronics, vol. 8, No. 2, pp. 387-394, Mar./Apr. 2002.

Park, et al., "Photodetection in the visible, ultraviolet, and near-infrared with silicon microdischarge devices," Applied Physics Letters, vol. 81, No. 24, pp. 4529-4531, Dec. 9, 2002.

Park, et al., : Arrays of silicon micro discharge devices with multicomponent dielectrics, Optics Letters, vol. 26, No. 22, pp. 1773-1775, Nov. 15, 2001.

Phillips, J.B. et al., "Thermal Modulation: A Chemical Instrumentation Component of Potential Value in Improving Portability," Field Analytical Chemistry and Technology, 1(1):23-29, 1996.

Quimby, et al., "Evaluation of a Microwave Cavity, Discharge Tube, and Gas Flow System of Combined Aas Chromatography—Atomic Emission Detection," Analytical Chemistry, vol. 62, No. 10, pp. 1027-1034, May 15, 1990.

Robinson, "The origins of electrical precipitation," Electrical Engineering, vol. 82, No. 9, pp. 559-564, Sep. 1963.

Shvartsburg et al., "Structural Elucidation of Fullerene Dimers by High-Resolution Ion Mobility Measurements and Trajectory Calculation Simulations," J. Phys. Chem. A 1997, 101, pp. 1684-1688.

Stevenson, Robert, "Wintergreen '97," The World of Separation Science, The 19th International Symposium on Capillary Chromatography and Electrophoresis, 11 pages.

Thompson, et al., "Ultraviolet Absorption Coefficients of $CO_2$, CO, $O_2$, $H_2O$, $N_2O$, $NH_3$, NO, $SO_2$, and CH, between 1850 and 4000 A," Journal of Geophysical Research, vol. 68, No. 24, pp. 6431-6436, Dec. 15, 1963.

Toker et al., "Design and development of a fiber optic TDI CCD-based slot-scan digital mammography system," X-ray Detector Physics and Applications II, Proceedings SPIE—The International Society for Optical Engineering, vol. 2009 (Jul. 13-14, 1993) pp. 246-252.

Whitman et al., "Double-Injection FIA Using First-Order Calibration for Multicomponent Analysis," Analytical Chemistry 63 (1991) pp. 775-781.

Young et al., "The Knudsen Compressor as an Energy Efficient Micro-Scale Vacuum Pump," 2nd NASA/JPL Miniature Pumps workshop, Pasedena, CA., 10 pages, Mar. 28, 2002.

* cited by examiner

| Applied Pot. V | Ion mol Fraction | Gas Velocities for Ls=Le cm/s | Ls cm/s | Re(Ls) - | Δp(Ls) psid | Qohmic mW | Ion+Flow Qvisc mW | Qgen mW | Qvisc+Qgen Qtotal mW | Qideal mW |
|---|---|---|---|---|---|---|---|---|---|---|
| *100 | 1.000E-12 | 0.01 | 0.00 | 0.000 | 0.000010 | 0.0000000 | 1.238E-12 | 0.000001 | 1.11E-06 | 1.238E-12 |
| Ion Radius, rion cm | 3.162E-12 | 0.04 | 0.00 | 0.000 | 0.000031 | 0.0000001 | 1.238E-11 | 0.000003 | 3.51E-06 | 1.238E-11 |
| *1.50E-08 | 1.000E-11 | 0.12 | 0.00 | 0.000 | 0.000097 | 0.0000002 | 1.238E-10 | 0.000011 | 1.11E-05 | 1.238E-10 |
| Cap.Radius, rc cm | 3.162E-11 | 0.37 | 0.01 | 0.001 | 0.000307 | 0.0000005 | 1.238E-09 | 0.000035 | 3.51E-05 | 1.238E-09 |
| *0.005 | 1.000E-10 | 1.18 | 0.02 | 0.002 | 0.000971 | 0.0000017 | 1.238E-08 | 0.000109 | 1.11E-04 | 1.238E-08 |
| | 3.162E-10 | 3.72 | 0.07 | 0.005 | 0.003072 | 0.0000053 | 1.238E-07 | 0.000346 | 3.51E-04 | 1.238E-07 |
| Field Length, Le cm | 1.000E-09 | 11.76 | 0.24 | 0.016 | 0.009715 | 0.0000168 | 1.238E-06 | 0.001095 | 1.11E-03 | 1.238E-06 |
| | 3.162E-09 | 37.20 | 0.74 | 0.050 | 0.030721 | 0.0000531 | 1.238E-05 | 0.003465 | 3.53E-03 | 1.238E-05 |
| *1 | 1.000E-08 | 117.62 | 2.35 | 0.159 | 0.097147 | 0.0001684 | 0.00012 | 0.010996 | 0.01 | 0.0001 |
| | 3.162E-08 | 371.96 | 7.44 | 0.502 | 0.307206 | 0.0005383 | 0.00124 | 0.035152 | 0.04 | 0.0012 |
| Tot.Cap.Length,Ls cm | 1.000E-07 | 1176.23 | 23.52 | 1.586 | 0.971472 | 0.0017605 | 0.01238 | 0.114973 | 0.13 | 0.0124 |
| *50 | 3.162E-07 | 3719.57 | 74.39 | 5.016 | 3.072064 | 0.0061508 | 0.12379 | 0.401686 | 0.53 | 0.1238 |
| | 1.000E-06 | 11762.30 | 235.25 | 15.863 | 9.714720 | *0.0252860 | *1.23797 | 1.651345 | *2.91 | *1.2379 |
| Eion, Ioniz.Energy eV | 3.162E-06 | 37195.66 | 743.91 | 50.163 | 30.720642 | 0.1383175 | 12.37871 | 9.033049 | 21.55 | 12.3787 |
| *70 | 1.000E-05 | 117623.02 | 2352.46 | 158.628 | 97.147201 | 1.0209592 | 123.78713 | 66.675372 | 191.48 | 123.7871 |

Drift Vel. in cm/s, vd= 461.747
NA, Avogadro Num. in 1/cm3= 2.8830E+19   *1
q,Electronic Charge in Cb= 1.6022E-19

*Figure 2*

Electron Affinities and Electron Configurations

| Element | Electron Affinity (kJ/mol) | Electron Configuration | Ionization Energies (kJ/mole) |
|---|---|---|---|
| H | 72.8 | $1s^1$ | 1300 |
| He | <0 | $1s^2$ | 2400 |
| Li | 59.8 | $[He]\,2s^1$ | |
| Be | <0 | $[He]\,2s^2$ | |
| B | 27 | $[He]\,2s^2\,2p^1$ | |
| C | 122.3 | $[He]\,2s^2\,2p^2$ | 1050 |
| N | <0 | $[He]\,2s^2\,2p^3$ | |
| O | 141.1 | $[He]\,2s^2\,2p^4$ | |
| F | 328.0 | $[He]\,2s^2\,2p^5$ | 1300 |
| Ne | <0 | $[He]\,2s^2\,2p^6$ | |

*Figure 4*

Comparison of Performance Between Pumps Based on Different Technologies

| Method | Base Unit Size x N mm3 | Frequency Hz | Power mW | Voltage V | Flow Rate cm3/min | ΔP psid |
|---|---|---|---|---|---|---|
| Theoretical Ion Drag | 10 x 0.25 x 1 = 2.5 | DC<br>DC | 1.26<br>1.65 | 1.41<br>401.41 | 9.7<br>9.7 | |
| MesoPump (el.-static, future) | 5x5x0.5x15 = 188 | 25 | 14 | 100 | 1.0 | 10 |
| MesoPump (el.-static, today) | 10x10x1x50 = 5000 | 3 | 25 | 150 | 1.0 | 10 |
| MesoPump (el.-static, today) | 10x10x1x50 = 5000 | 3 | 25 | 150 | 1.0 | 10 |
| Piezo-Electric (fraunhofer) | 7x7x1.1x7x14 = 5282 | 100 | | 98 | | |

*Figure 8*

Temperature Dependence of Ion Concentration ⟵ 23

| Temper. T in K | Ion Aff. Energy E(-) in J/mol 100,000 exp(-E/RT) | Ionizat.Energy E(+) in J/mol 1,000,000 exp(-E/RT) |
|---|---|---|
| 600 | 2.239E-09 | 3.169E-87 |
| 1500 | 3.468E-04 | 2.514E-35 |
| 2000 | 2.541E-03 | 1.123E-26 |
| 2500 | 8.395E-03 | 1.739E-21 |

*Figure 9*

MICRO ION PUMP

The present patent application claims priority as a continuation-in-part of co-pending U.S. Nonprovisional Patent Application Ser. No. 10/750,483, filed Dec. 31, 2003, and entitled "GAS IONIZATION SENSOR", which is hereby incorporated by reference in its entirety in the present application. The present patent application claims priority as a continuation-in-part of co-pending U.S. Nonprovisional Patent Application Ser. No. 10/749,863, filed Dec. 31, 2003, and entitled "MICRO-PLASMA SENSOR SYSTEM", which is hereby incorporated by reference in its entirety in the present application.

BACKGROUND

The present description pertains to pumps and particularly to gas pumps. More particularly, it pertains to micro pumps.

Related-art gas pumps for microanalytics are bulky, comprise mechanical actuators that are prone to wear and limit their service life, and create undesirable flow pulsations that need to be dampened via bulky buffer volumes. The cost to fabricate and assemble such mechanical actuation pumps (regardless of whether they are based on electromagnetic, piezo-electric or electro-static forces) is high and contributes to their high price.

SUMMARY

The present pump avoids related-art shortcomings by generating a steady gas flow, which is driven by viscous drag created by a small volumetric fraction of large (relative to the electrons), in-situ-generated ions, which then drift in a steady applied electric field. The uniformity of the applied DC electric fields and operation of such pumps is favored by the scale and length/diameter ratio of MEMS or micro channels.

BRIEF DESCRIPTION OF THE DRAWING

FIG. 2 is a table of an example of ion drag pump flow and energy characteristics;

FIG. 4 is a table of electron affinities and electron configurations for some elements of interest;

FIG. 8 is a table comparing pump performances based on different technologies;

FIG. 9 is a table of temperature dependence of ion concentration;

DESCRIPTION

Figure 1:
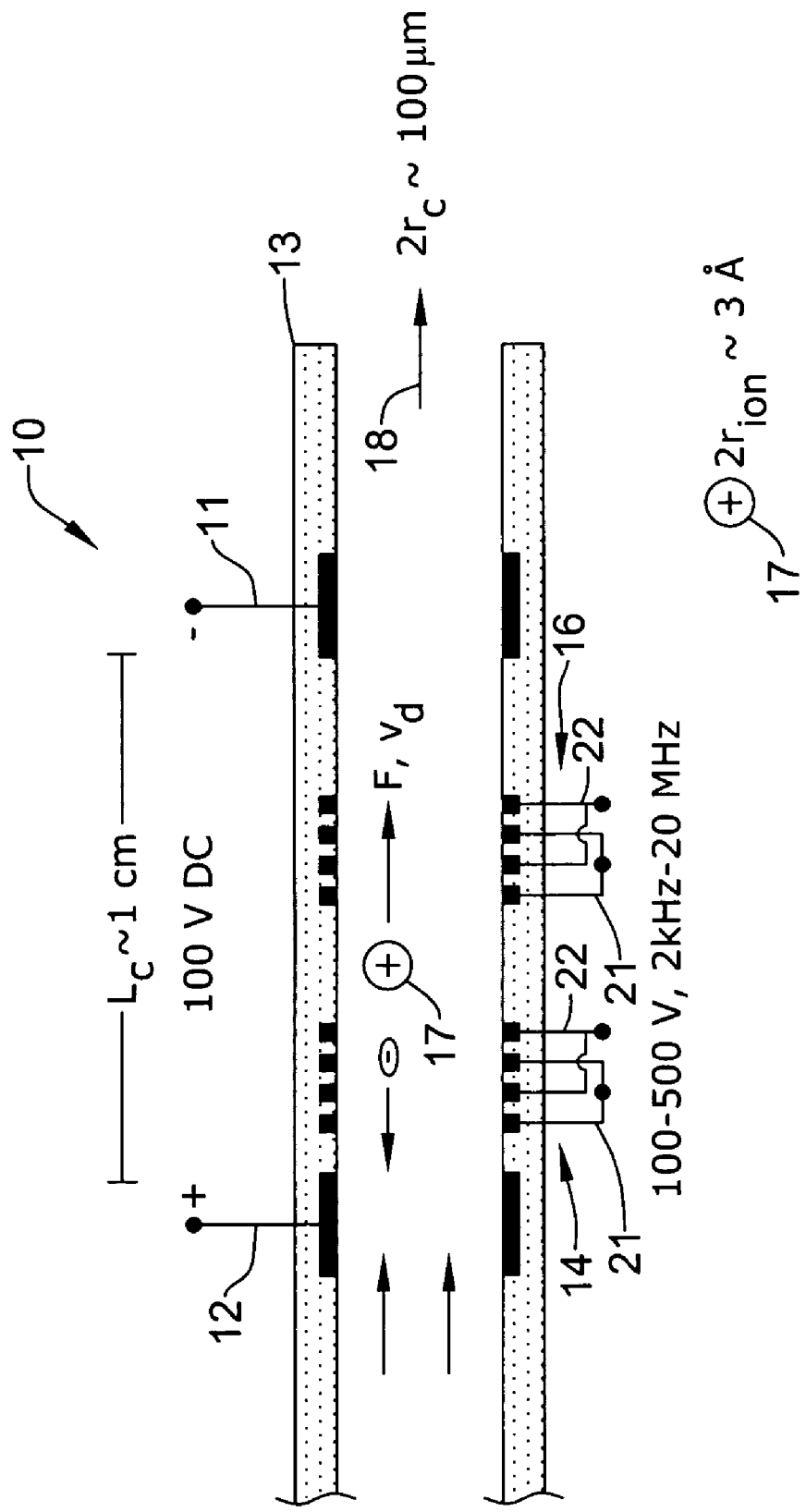
FIG. 1 is a cross-sectional view of an ion drag pump for brief explanation of the principle of operation of such pump.

FIG. 1 is a cross-sectional view of a pump 10. High frequency micro discharge devices (MDDs) 14 and 16 may generate ion-electron pairs. Relatively larger ions 17 may drift towards the (−) electrode 11 and drag neutral molecules along. The ion-drift pump 10 may work on the principle of viscous drag of ions attracted by an applied e-field, so that their cumulative surface drags the neutral molecules along to the extent of establishing a balance between this drag and the drag between the induced flow 18 and the capillary tube (or MEMS channel) wall 13. The former may be given by the mobility, number density and volume of the ions in the applied e-field (Stokes' Law), whereas the latter may be given by Poiseuille's Law of capillary flow. The term "fluid" may be used as a generic term that includes gases and liquids as species. For instance, air, gas, water and oil are fluids.

Stokes' Law relates particle radius, r, particle velocity, v, and fluid viscosity, $\eta$, to viscous shear force, $F_v$, where $$F_v = 6\pi \cdot \eta \cdot v \cdot r.$$

If this particle 17 is charged it also experiences an electrostatic force, $F_e = E \cdot q$. The associated drift velocity of a particle of charge, q, mass, m, experiencing an average time between collisions, $\tau$, and subjected to the force of an electric field, E, is $v = v_d$, where for $m(N_2) = 0.028$ kg/mole/$N_A$ and $$\begin{aligned} v_d &= q \cdot E \cdot \tau/m \\ &= 1.6022 \cdot 10^{-19} \cdot 1 \cdot 1.34 \cdot 10^{-10}/(0.028/6.022 \cdot 10^{23}) \\ &= 0.000462 \text{ m/s per V/m or } 4.62 \text{ cm}^2/(Vs) \end{aligned}$$

or 462 cm/s if one applies 100 V to the (+) electrode 11 and (−) electrode 12 spaced at about 1 cm.

To arrive at the above $v_d$, $\tau = 6.7 \cdot 10^{-6}/50,000 = 1.34 \cdot 10^{-10}$ sec may be used, based on the average velocity of $N_2$ molecules in air of v=50,000 cm/s, and where $\tau$=time between collisions=$\lambda/v_T = \lambda/(3kT/m)^{0.5}$, $m = 28/N_A$=kg-mass of a $N_2^+$ charge carrier, $v_T$=thermal velocity and $\lambda$=mean free path=$6.7 \times 10^{-6}$ cm at 1 atm, or generally, $\lambda = 0.005/p$, with p in Torr and $\lambda$ in cm at ambient conditions, $N_A = 6.022 \cdot 10^{23}$=Avogadro Number of molecules per mole, the Boltzmann constant, $k = 1.3807 \cdot 10^{-16}$ erg/K, and the elemental charge value of $q = 1.6022 \cdot 10^{-19}$ coulombs.

The viscous shear force on the capillary wall 13 caused by fluid flow is derived from Poiseuille's Law, which relates volume flow to pressure drop: $V = \pi r_c^2 v = \pi \cdot \Delta p \cdot r_c^4/(8 \cdot L_c \cdot \eta)$, so that $F_c = \Delta p \cdot \pi r_c^2 = 8 \pi \cdot \eta \cdot v \cdot L_c$.

To equate the two forces, one may need to make an assumption on the concentration of ions. For v=100 cm/s, $r_c = 0.0050$ cm and for a $x_{ion} = 10$ ppb concentration of ions leads to a current of $$q \cdot \pi r_c^2 \cdot v \cdot x \cdot N_A^* = 1.6022 \cdot 10^{-19} \cdot \pi \cdot 0.0050^2 \cdot 100 \cdot 10^{-8} \cdot N_A = 0.0232 \, \mu A.$$

The associated power for an applied potential of 100 V is Q=2.32 µW. The number of traveling ions within the L=1 cm e-field section is $$N = N_A/V_M(T_o/T) \cdot x_{io} \cdot \pi r_c^2 \cdot L_c = 6.022 \cdot 10^{23}/22415(T_o/T)$$
$$10^{-8} \cdot \pi \cdot 0.0050^2 \cdot 1/=19,660,000 \text{ ions,}$$

while the total number of molecules in $L_c$ is $N_A^* = N_A/V_M(T_o/T) = 2.883 \cdot 10^{19}/\text{cm}^3$.

One may determine the achievable macroscopic flow velocity, $v_c$, by equating the ion drag force by N ions, $F_{ion}$, with that of capillary flow in the same length of capillary 13, $L_c$, with the force $F_c = \Delta p \cdot \pi r_c^2$ and set $F_{ion} \equiv F_c$, and remembering that ionic friction is related to $v_d$, but that ionic current relates to $v_c + v_d$, where $$F_{ion} = 6\pi \cdot \eta \cdot v_d \cdot r_{ion} \cdot x_{ion} \cdot N_A^* \cdot \pi r_c^2 L_c \equiv F_c = 8\pi \cdot \eta \cdot v_c \cdot L_c; \text{ and}$$

one may get, with $r_{ion} = 1.5 \cdot 10^{-8}$ cm, $v_d(100 \text{ V/cm}) = 461.6$ cm/s:

$$v_c = (6\pi/8) \cdot v_d \cdot x_{ion} \cdot r_{ion} \cdot N_A^* \cdot r_c^2 = (2.3562) \cdot 461.7 \cdot 10^{-8} \cdot 1.5 \cdot 10^{-8} \cdot 2.883 \cdot 10^{19} \cdot 0.0050^2 = 117.6 \text{ cm/s},$$

for 10 ppb ions and 100 V/cm in the 100 μm capillary.

Table 20 of FIG. 2 shows an ion-drag pump flow and energy characteristics. It lets a reader change the star-marked inputs of applied voltage, V, $r_{ion}$, $r_c$, and both lengths of capillary 13 at which the field is applied and the total system's capillary length, $L_s$, which determines $\Delta p$ for a given $v_c$. The rows in Table 20 then correspond to variations in the unknown and assumed unipolar ion concentration, which then determine the macroscopic viscous flow in a capillary of length $L_c$ and in one of length $L_s$, which results in a much smaller $v_c$ due to the much larger and also-listed $\Delta p$.

The table 20 data show that, barring minor variations in the values used above, this method of generating flow may work well, and with a very small concentration of ions, provided that one does not run into electron-attachment or space charge effects and can maintain electric neutrality as one pulls the heavy ions through the gas. However, this ion drift spectrometry may be leveraging, which can be used as a gas detector.

Figure 3:
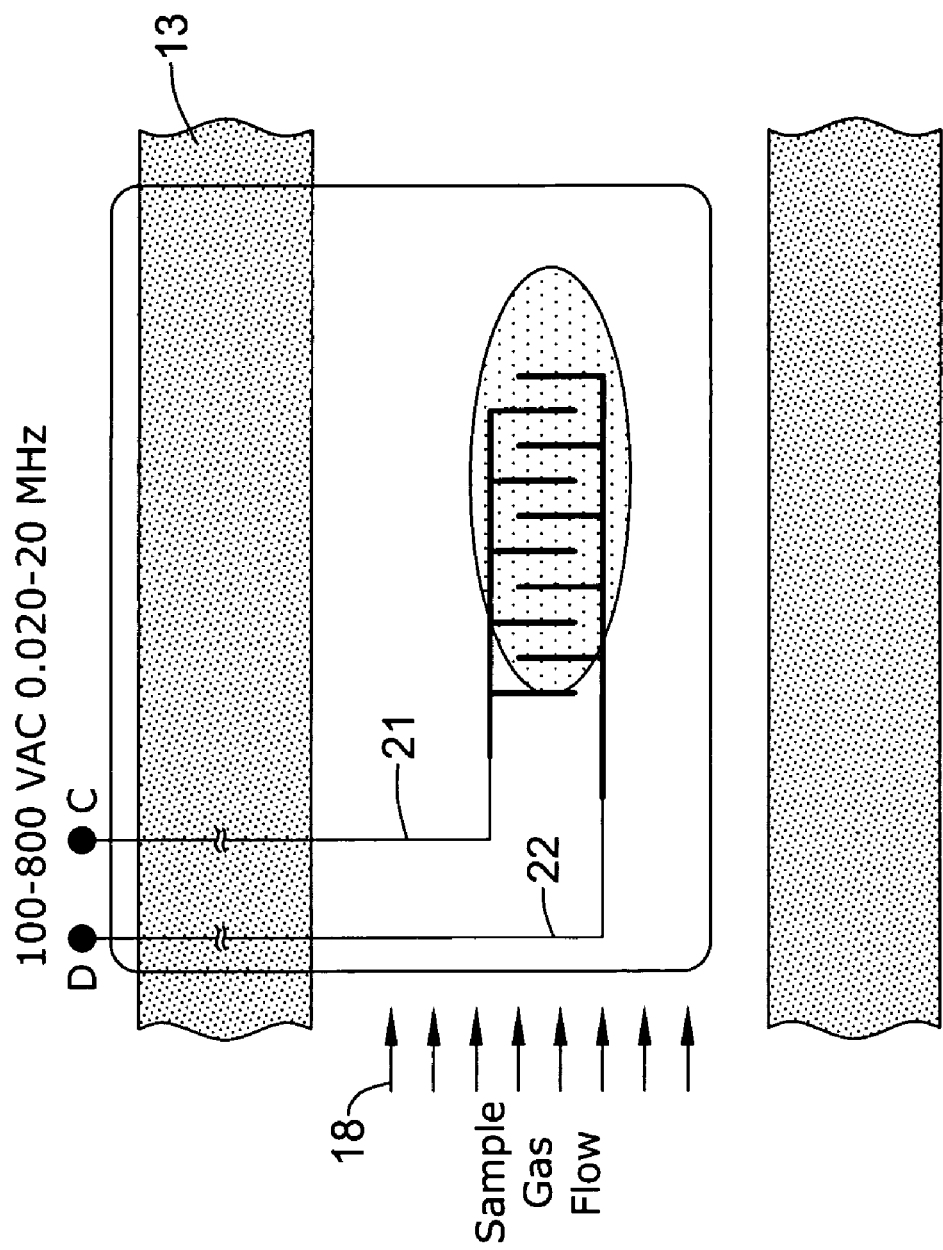
FIG. 3 is an example of an interdigited example of a micro discharge device that may be used in the pump of FIG. 1.

As one increases the intensity of the fields applied to the MDDs (microdischarge devices) 14 and 16 for ion generation, which are drawn into FIG. 1 as multiple sets of interdigitated electrodes 21 and 22 akin to those illustrated in FIG. 3; the rate of ion generation, their concentration, their collective drag and the resulting macroscopic flow velocity may increase until reaching a value close to that of the drift velocity, which in turn is controlled by the applied DC field of MDD 14 shown in FIG. 1. However, as such overall gas velocity, $v_c$, increases, it does not reach or exceed the ion drift velocity, $v_d$, which just adds to the top or continues to ride on top of gas velocity, $v_c$.

As the DC field is increased, changed or switched off, the macroscopic flow changes within fractions of a millisecond and may thus be used to control and/or pulse the flow in the second stage of a μGC-μGC analyzer. μGC may be micro gas chromatography.

Although conceived for use with gases, the easy availability of ions in liquids may lend itself to the use of pump 10 for liquid fluids also but less well, due to the much smaller difference between positive and negative ions (no free electrons) than between the mostly positive ions and the electrons in gases.

To determine the actual flow velocity that results from balancing the ion-drag action force and the viscous force offered by the flow in a capillary 13 of length, $L_{cs}$, one may set $F_{ion} \equiv F_c$, and therefore obtain $$6\pi \cdot \eta \cdot v_d \cdot r_{ion} \cdot N_{ion} = 8\pi \cdot \eta \cdot v_c \cdot L_{cs},$$

and numerically with $$r_{ion} = 1.5 \cdot 10^{-8} \text{ cm}, x_{ion} = 10 \text{ ppb}, v_d(100 \text{ V/cm}) = 461.6 \text{ cm/s},$$

$$L_{ce} = 1 \text{ cm}, L_{cs} = 50 \text{ cm and } r_c = 0.0050 \text{ cm},$$

-continued $$v_c = (6\pi/8) \cdot v_d \cdot x_{ion} \cdot r_{ion} \cdot N_A^* \cdot r_c^2 \cdot L_{ce}/L_{cs},$$

$$= (2.3562) \cdot 461.7 \cdot 10^{-8} \cdot 1.5 \cdot 10^{-8} \cdot 2.883 \cdot 10^{19} \cdot 0.0050^2$$

$$= 117.6 \text{ cm/s}.$$

This flow may increase with $v_d = q \cdot E \cdot \tau/m$, $x_{ion}$, $r_{ion}$ and $L_{ce}$, while it decreases as $L_{cs}$ is lengthened. Additional parameters are shown in table 20, especially those that relate to energy consumption.

The usefulness of this ion-drag pump may depend on the density and life of the generated ions, the differentiation in size or asymmetry between positive and negative charge carriers, and the asymmetric positioning and shape of the ion drift e-field electrodes.

By providing such essentials, the charge carriers may be able to drive flow of the neutral molecules, not just through its own e-field section but through and against a useful "load", i.e., against the flow restriction of a practical flow system as, e.g., in a GC or μGC of column length, $L_{cs}$. For practical and variable inputs such as 100 V/cm DC field, ion size (assumed enhanced by the attachment of polar molecules like water and a range of ion mole fractions, $x_{ion}$, (inputs are highlighted with stars), Table 20 lists the achievable flow velocities without load ($L_{cs} = L_{ce}$); and for a useful load the flow velocities, $v_c$, the Reynolds Numbers, Re, viscous pressure drops, $\Delta p_e$, and the dissipated powers and total power and efficiencies, using as a reference the ideal or theoretical power to move the gas against the listed pressure head.

An additional important consideration is the amount of power needed to not only draw and collect the ions, but to also generate and regenerate them as they drift and recombine along the e-field. It may be assumed in Table 20 that one would need to regenerate ions 99 times within the moving gas volume in the e-field. This may be partly redundant with the fact that the practical energy for generation of ions exceeds the theoretical ionization energy by a factor of 4 to 6, so that the textbook ~10 to 12 eV (see table 21 of FIG. 4, using eV×96600 Cb/mole for conversion to joules) becomes 60 to 70 eV in practice. The energy dissipations of the ion pump may thus be composed of the following elements: 1) Ionic drift viscous friction loss in the gas, which drives all, $Q_{iondrag} = F_v \cdot v_{ion} = 6\pi \eta v_{ion}^2 \cdot r_{ion} \cdot N_{ion}$; 2) Gas flow viscous friction loss, $Q_{gas} = F_c \cdot v_c = 8\pi \cdot \eta \cdot v_c^2 \cdot L_{cs}$; 3) Electric, ohmic power dissipation, $Q_{ohmic} = U \cdot I = U \cdot q \cdot N_{ion}(v_{ion} + V_{gas})$; 4) Ion generation and (99%) regeneration, $Q_{gen} = (1+99) \cdot E_{ion} \cdot N_{ion} \cdot (v_{ion} + v_{gas})$; and 5) Work on moving (assumed incompressible) gas through the $\Delta p$, $Q_{ideal} = \int V_F(p) dp$ is $\sim \pi \cdot r_c^2 \cdot v_{gas} \cdot \Delta p$.

Table 20 of FIG. 2 shows data, indicating that even if one needs to regenerate the ion-electron pairs 99 more times due to recombination, in order to maintain an exemplary ion concentration of $x_{ion} = 10^{-6}$, the ion pump may achieve ~50% efficiency. This is for reference conditions of E=100 V/cm, $L_{cs}$=50 cm, $r_{ion}$=1.5 Å, and $r_c$=50 μm. The table data may reveal certain characteristics: as ion concentration increases, so do pumping velocity, Re, $\Delta p$, and individual Qs, but also efficiency; the power dissipated via the ionic current and applied DC voltage, $Q_{ohmic}$, may be ~100 times lower than $Q_{visc}$, but may not have to be used in the computation of $Q_{total}$, which is based on the sum of the viscous dissipation of ions and capillary flow+ion generation and regeneration energy.

Changing input parameters may reveal further features of the pump and its present model: 1) Increasing the effective ion radius by a factor of 2 increases efficiency at $x_{ion}$=1 ppm from 42.5 to 68.8%; 2) The needed generation power is only 1.65 mW for $E_{ion}=70$ eV and 99% regeneration rate; 3) Reducing the e-field by 2 times decreases flow by 2 times and efficiency from 42 to 27%; and 4) Reducing the capillary length by 2 times doubles the flow velocity, maintains the pressure drop constant and increases efficiency to 52.5%.

As mentioned above, an application a practical ion-drag pump may depend on the ability to configure and operate MDDs to generate the needed ion concentrations and asymmetries. By configuring MDDs 14 and 16 in series and parallel, the desired flow and pump pressure head may be achieved.

Achieving advantageous energy efficiencies obtained by the present model may depend of the actual number and amount of power the MDDs needed to move the sample gas. Descriptions of macroscopic ion-drag pump systems may show reduced efficiency as dimensions are reduced, but may be strongly dependent on the involved type of ion generation.

Figure 5:
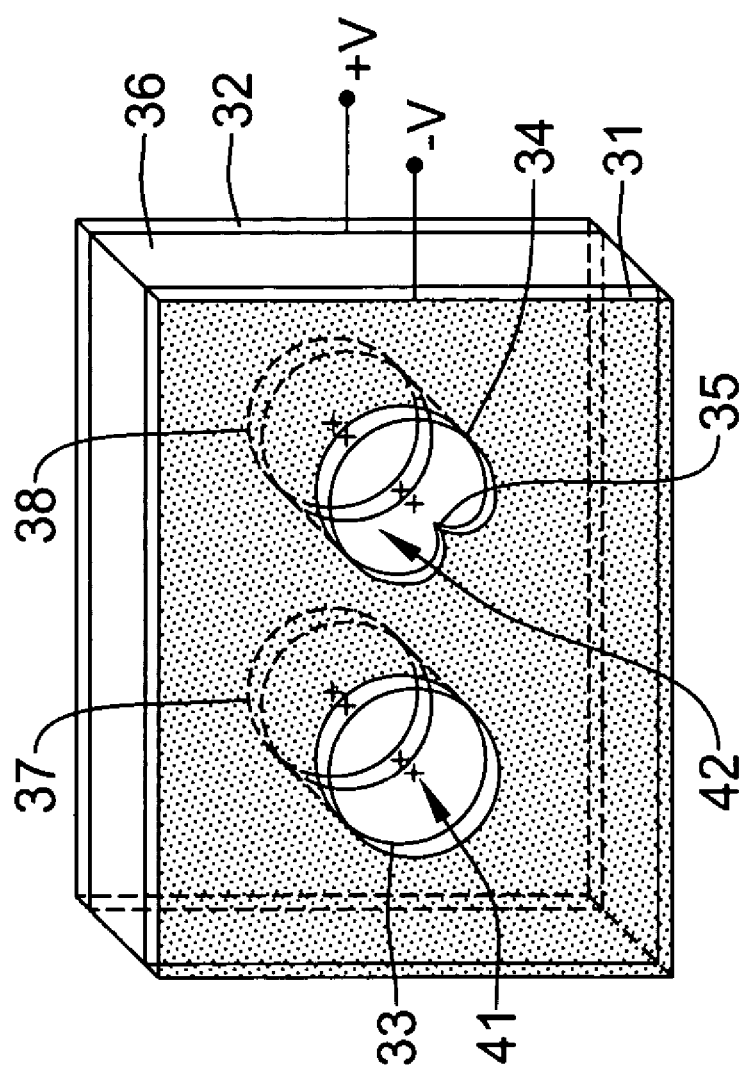
FIG. 5 is an illustration of two elements of an array of micro discharge devices for an ion drag pump.

One type of MDDs that may be well suited for operation of micro-scale pumps may be those stabilized in arrays of orifices, as used for UV light generation, and sketched out in FIG. 5, with TBD orifice size and shape, electrode film thickness, edge smoothness and pattern; only two contacts are needed to operate many MDDs (100 to 10,000). FIG. 5 shows two elements 31 and 32 of an array of MDDs for ion drag pumping through the orifices 33 and 34. Symmetry variation may be implemented via electrode shape or thickness to create a source of corona generation. Orifice 33 may have a thin or sharp edge to make it favorable for emission and causing a corona of ionization to provide ions. On the other hand, orifice 34 in electrode 31 may have a projection or sharp point 35. Orifice 34 may instead have numerous projections or sharp points 35 for causing a corona and resultant ionization. Even though there are two examples of orifices 33 and 34 in plate 31, there may be thousands of them in the electrode plate of an ion pump. Corresponding to orifices 33 and 34, there may be orifices 37 and 38 in electrode plate 32 aligned with orifices 33 and 34, respectively. Between electrode plates 31 and 32 is an insulator material 36 with holes 41 and 42 connecting the respective orifices. Holes 41 and 42 may have dimensions or diameters about the same as those of orifices 33, 37 and 34, 38, may be situated in the insulation layer 36 connecting corresponding orifices in opposing electrode plates 31 and 32.

Figure 6:
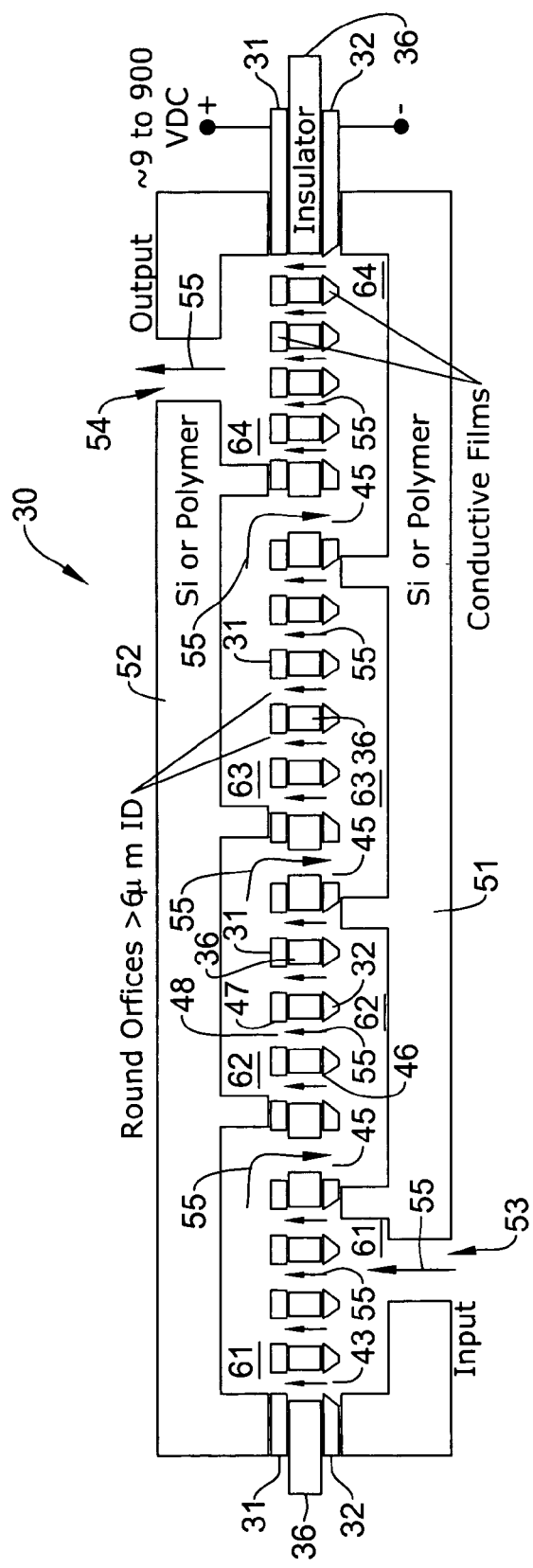
FIG. 6 shows an illustrative example of an ion drag pump.
Figure 7:
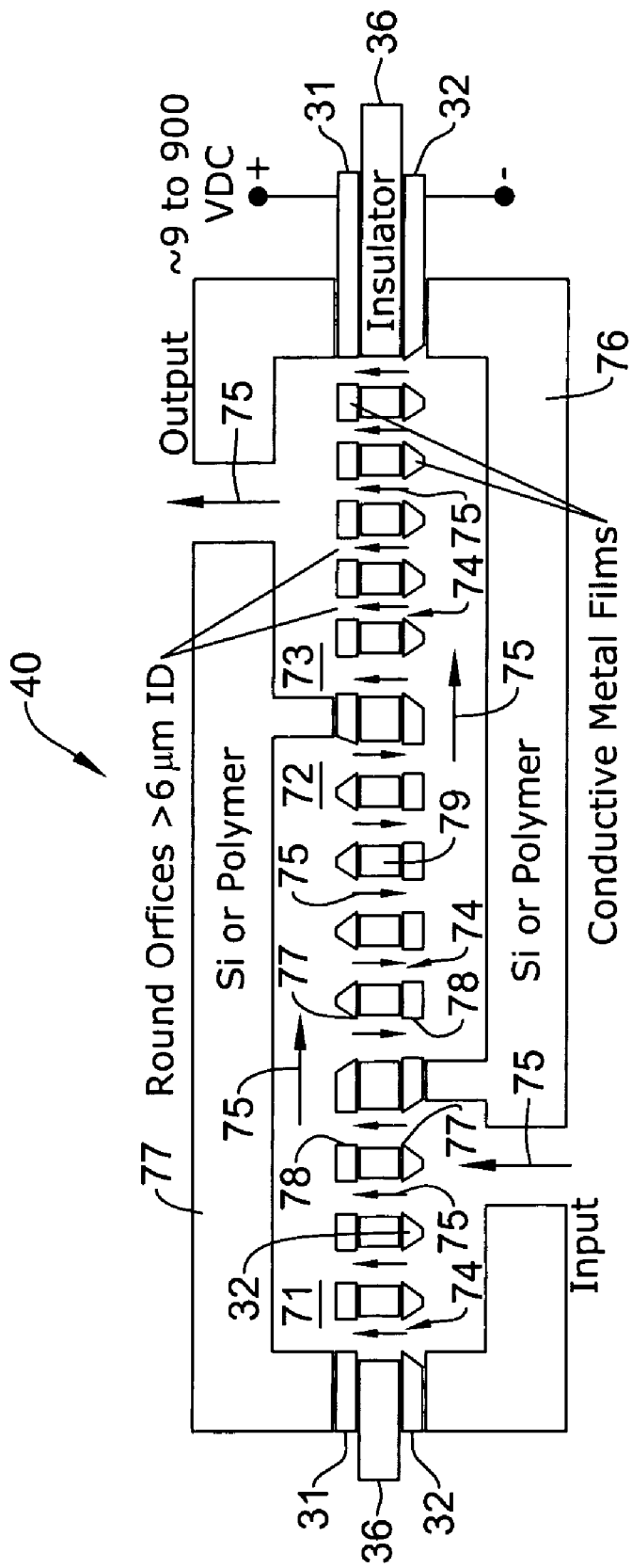
FIG. 7 shows another illustrative example of an ion drag pump.

Several versions with a small exemplary number of parallel and series orifice-MDDs in an array on a thin-film dielectric are presented in FIGS. 6 and 7. Note that the electro-active orifices are the ones with a small inside diameter, whereas the larger ones serve to guide the flow to the next pump-stage, located on the same side of the insulator as the input side of the first stage.

FIG. 6 is a cross-sectional sketch of an ion drag pump 30 having several sets of parallel pumping elements 43 in a series of stages of the pump 30. Sets of elements 43 may be in stages or sub-chambers 61, 62, 63 and 64 which may be connected in series by channels or holes 45 through layers 31 and 32, and insulator 36. The insulator may protrude into channel 45 so as to deter discharge in that channel. The orifices 46 and 47, and holes 48 may be round or some other shape. The electrode layers 31 and 32 may be conductive films to provide a corona having a polarity. Each element or hole 45 itself may be designed to be a pumping element with the corona polarity switched for moving the fluid in the other direction relative to the direction of flow through elements 43. Each element 43 may have an orifice 46 that resembles orifice 33 or 34 of FIG. 5. The orifices 46 and 47, and the holes 48 may have an inside diameter of about 6 microns or more. Also, each element 43 may have an orifice 47 that resembles orifice 37 or 38 of FIG. 5. Between orifices 46 and 47 is a hole or channel 48 in the insulation 36 which may resemble the hole 41 or 42 in FIG. 5. As many parallel and staged elements 43 and 44, respectively, as needed, may be fabricated to achieve the desired flow and Δp.

At the thin or sharp edged or pointed orifice 46, a corona discharge may be an electrical discharge brought on by the ionization of a fluid surrounding a conductor, which occurs when the potential gradient or concentrated field exceeds a certain value, in situations where sparking is not favored. In the negative corona (generated from high-voltage applied to a sharp point or ridge), energetic electrons are present beyond the ionization boundary and the number of electrons is about an order of magnitude greater than in the positive corona. Both positive and negative coronas can generate "electric wind" and drag neutral molecules towards a measurable flow. The voltage that may be applied to plates 31 and 32 may be a value from about 9 volts to about 900 volts DC. The plus polarity of the power supply may be applied to plate 31 and the negative polarity or ground of that supply may be applied to plate 32. Insulator layer 36 may be of a dielectric material and have a thickness sufficient to prevent arching of voltage between electrode plates or films 31 and 32.

On a first side of the elements 43 may be a chamber side 51 for containing the fluid that may be pumped through pump 30. On the other side of the elements 43 may be a chamber side 52. An input port 53 for the entry of fluid into pump 30 may be towards one end of the chamber side 51 and pump 30. Sides or walls 51 and 52 may be made from silicon, a polymer or other appropriate material. An output 54 for the exit of fluid out of pump 30 may be towards other end. A flow of a fluid 55 may enter input port 53 into a chamber of the first stage of pump 30. The fluid 55 may flow from input 53 through elements 43 of a first stage or sub-chamber 61, second stage or sub-chamber 62, third stage or sub-chamber 63, fourth stage or sub-chamber 64 and out of pump 30 through exit port 54.

An ion pump may have an insulating layer 36, a first conductive layer 32 situated on a first side of the insulating layer 36, and a second conductive layer 31 situated on a second side of the insulating layer 36. There may be openings 46 situated in the first conductive layer 32, the insulating layer 36 and the second conductive layer 31 thereby forming elements or channels 43 having first and second discharge device electrodes, respectively. An enclosure, such as enclosure 51 and 52 of FIG. 6, may contain the channels 43 and have an input port 53 proximate to the first conductive layer 32 and an output port 54 proximate to the second conductive layer 31. A fluid (preferably gas) 55 in the enclosure may be transported between the input 53 and output 54 of that enclosure, by being forced through the channels 43.

The openings 46 on the first conductive layer 32 may have a sharp-like configuration, and the openings 47 on the second conductive layer 31 may have a non-sharp-like configuration. This arrangement provides for predominant generation of in-situ ions proximate to the sharp-edged conductor openings 46. The ions then bear predominantly the polarity of those sharp edges, which then may induce a fluid 55 flow of neutral molecules as a result of the force and viscous drag of those predominant ions.

The sharp conductor of opening or orifice 46 may provide an electrical discharge with conductive nanotube whiskers. The nanotube whiskers may be operated in a cold cathode field emission mode. The nanotube whiskers may also operate in a corona discharge mode. The electrical discharge may be energized by one of DC and AC applied voltages. The sharp conductive opening or electrode for providing an electrical discharge may consist of thin-film material. The conductive electrode material such as thin film material for providing an electrical discharge may be operated in a cold cathode field emission mode. Or the conductive electrode material such as the thin film material for providing an electrical discharge may be operated in a corona discharge mode.

The sharp edges of the predominant discharge polarity electrodes of openings or orifices 46 may consist of 10- to 100-nm-thick films of conductive material, and the film thickness of the non-predominant electrodes of openings or orifices 47 may be at least 10-100 times thicker and rounded at its inner diameter edge.

The openings or orifices 45 and 46, and holes 48 may be fabricated via one of etch, laser-drill, mechanical stamping and combination of these. The openings may be sized for a ratio of axial length (=non conductive film thickness) to inner diameter, R, of maximize the performance of the pump, so that approximately $1 \leq R \leq 10$, and the film thickness for the non-conductive spacer is about $6 \, \mu m \leq S \leq 100 \, \mu m$.

The pump may consist of as many consecutive, i.e., serial, stages, L, (e.g., stages 61, 62, 63 and 64) and applied voltage, U, as needed to achieve the desired total pressure head, $\Delta p_t = n \cdot \Delta p$, where the achieved pressure head at each stage is about $\Delta p$, with due allowance for the changes in absolute pressure, gas volume (due to its compressibility) and temperature at each stage, which entails changes in pump effectiveness and capacity at each stage. The number of openings, stages, n, and applied voltage, U, may be chosen so that the desired total pumping volumetric rate and total pump head pressure can be achieved, with due allowance for the pressure drop through the pump itself (requiring a number of openings, $n_o$) and through the (analyzer) load itself. The number of openings may be increased by a factor $\alpha = n/n_o = \Delta p_o/(\Delta p_o - \Delta p_L)$, where $\Delta p_o$=ion pump pressure head without a load and $\Delta p_L$=pressure drop through the load, with preferably $\Delta p_o \sim 2 \cdot \Delta p_L$.

Rapid control of sample gas flow in the pump may be enabled upon resetting the applied fields, to, e.g., achieve small gas pulses/injections of sample/analyte into micro-GC columns, as in the second stage of a GC-GC system or the second part of a separation column of a second material. The ion pump may be operated like a valve by adjusting the applied voltage to the conductive electrodes to just oppose and balance external flow or pressure drivers. The sharp-edged electrode or sharp-like openings may be recessed to a larger ID (inner diameter) than the ID of the insulating layer, by a radial distance equal to about 10 to 20% of the insulating layer radius, to enable removal of the non-predominant polarity ions before the remaining predominant ions enter the ID of the openings in the insulating layer.

The present pump may be a gas pump without moving parts, driven by the force and drift caused by an electric field on ions that are generated inside the pump. Although "normally open" when not energized, the pump may maintain zero or positive flow when energized. The simple design of the pump consists of a central insulating layer that supports a top and a bottom electrode with many parallel openings for operation of asymmetric corona discharges.

FIG. 7 is a cross-sectional sketch of a set of parallel and series pumping elements of an ion drag pump 40. Pump 40 may be fabricated with three stages 71, 72 and 73 and as many parallel elements 74 as needed to achieve the desired flow of a fluid 75. Elements 74 may each have an orifice 77 in electrode plate 32 of stages 71 and 73 and in electrode plate 31 of stage 72. Elements 74 may each have an orifice 78 in electrode plate 31 of stages 71 and 73 and in electrode plate 32 of stage 72. Orifice 77 may resemble orifice 33 or 34 of FIG. 5. Orifice 78 may resemble orifices 37 and 38 of FIG. 5. Connecting the corresponding orifices 77 and 78 may be a hole 79 through the insulator 36. Hole 79 may resemble hole 41 or 42 in FIG. 5. The orifices 77 and 78, and the holes 79 may have an inside diameter of about 6 microns or more.

The pump 40 chamber may be formed with chamber sides or walls 76 and 77 which may be fabricated from silicon, a polymer or other appropriate material. Between stages 71 and 72 and between stages 72 and 73 of pump 40, the corona polarity may be switched to avoid the extra flow switch 45 of pump 30 in FIG. 6. The vacuum pump 40 may remain at three stages but one may increase the number of parallel elements 74 as needed to achieve the desired flow. Also, pump 40 may feature an increasing number of elements per stage as the gas expands and requires an increased volume flow.

The design of pump 40 may do away with the extra routing of the sample gas being pumped. Other tradeoffs may be made relative to pump 30 of FIG. 6. Pump 40 may use the same material for both electrodes. Or a pattern of depositions of a first material may be used for the sharp-tipped corona emitter (i.e., ionizer) and a second material for the collector.

Listed as follows is the nomenclature of some common physical parameters relative to the present description. E is electric field; E=U/s, in volts/cm; $E_{ion}$ is energy of formation of ions; F is force of electrostatic field, $F_e$, of ionic viscous drag, $F_{ion}$, or of viscous capillary flow, $F_c$; $L_c$ is length of the capillary, in the applied e-field, $L_{ce}$, and of the whole system, $L_{cs}$, in cm; λ is mean free path between collisions, in cm; N is number of ions in the length of capillary between electrodes, $N = x_{ion} \cdot N_A^* \cdot \pi \cdot r_c^2 \cdot L_{ce}$; $N_A$ is Avogadro number in mol$^{-1}$; $N_A^*$ is Avogadro number in cm$^{-3}$; r is radius of capillary, $r_c$, or ion, $r_{ion}$; T is temperature in K; τ is time between collisions $\tau = \lambda/v_T = \lambda/(3 \, kT/m)^{0.5}$, in s; x is molar or volumetric fraction of ions, $x_{ion}$, or molecules, x; v is velocity—1) Ion drift relative to fluid, $v_{ion}$; and 2) Macroscopic capillary flow, $v_c$, in cm/s; $v_{ion}$ is velocity of ion drift relative to fluid, total ion velocity=$v_{ion}+v_c$, but friction loss $\sim v_{ion}$; V is volume in cm$^3$; $V_F$ is volumetric flow in cm$^3$/s; $V_M$ is volume of one mol of gas, $V_{Mo}$ under 1 atm and 0° C. conditions.

Some of the features of the pumps 10, 30 and 40 may include: 1) Use of in-situ-generated ions to induce macroscopic gas flow in a small channel, as observed in the deflection of flames when a high electric field is applied (electric wind effect), which leverage the large size difference between bulky positive ions and ~1000 times smaller (mass of) electrons; 2) Generation of such ions via suitably distributed MDDs, typically energized by electroless discharges operating in the 2 kHz to 20 MHz frequency range; 3) Taking advantage of the high frequency MDD to eliminate pump pulsations plaguing traditional mechanical pumps; 4) Applying non-symmetrical AC voltage and power to the ion-accelerating ions, in order to also use electroless operation, so that the negative electrode attracting the mostly positive and heavy ions gets most of the fractional "on"-time; 5) Merging the MDD for ion generation with the set of electrodes used to generate ion drift, whereby the above non-symmetrical approach is used for both generation and ion drift/acceleration; 6) Rapid control of gas flow upon resetting the applied fields, to, e.g., achieve small gas pulses/injections of sample/analyte into micro-GC columns, as in the second stage of a GC-GC system; and 7) Operation of the ion pump as a valve by adjusting the applied voltage to just oppose and balance external flow or pressure drivers.

The advantages of the pumps 10, 30 and 40 over related-art pumps may include: 1) Elimination of or much reduced flow pulsations; therefore elimination of buffer volumes; 2) Reduced mechanical noise; 3) Smaller size, lower power (see table 22 of FIG. 8), no mechanical wear of moving pump parts and longer life; and 4) Lower cost and maintenance, and greater reliability.

Comparison of performance parameters between an ideal, theoretical pump and an actually operating one may be made. The present pumping approach has compactness and low power consumption. A comparison to other pumping schemes to achieve 235 cm/s in a 100×100 µm duct, i.e., 1.41 cm$^3$/s against Δp of 9.7 psi, is shown in table 22 of FIG. 8. As shown, the ion drag pump, not only may pump a continuously variable rate of sample gas without ripple, but may be readily rate-controlled via adjustments in the drag voltage, occupy 100 to 1000 times less space, and consume about 10 times less power than the next best electrostatic-mechanical pump. This next-best pump may be a mesopump, as disclosed in U.S. Pat. Nos. 6,106,245; 6,179,586 B1; and 6,184,607 B1.

Energies are needed to generate ions. Listed are two sets of examples which may show that the generation of positive gas ions is roughly 10 times higher than that for negative electrons. The table 21 in FIG. 4 shows electron affinities and electron configurations for the first ten elements in the Periodic Table. FIG. 9 shows a table 23 showing temperature dependence of ion concentration.

Figure 10:
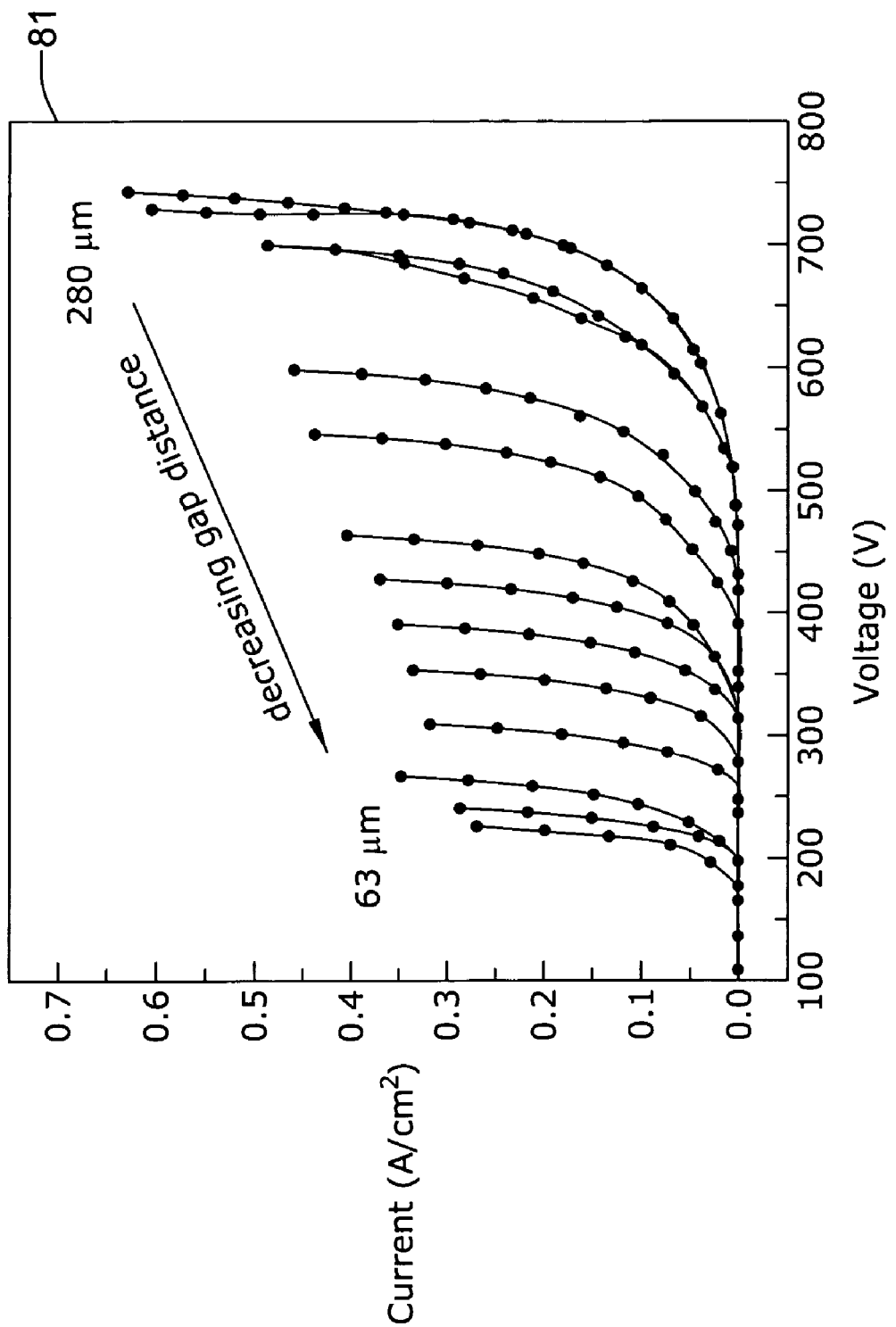
FIG. 10 is a graph about electron cold-cathode emission from a carbon nanotube in terms of current density versus applied voltage.
Figure 11A:
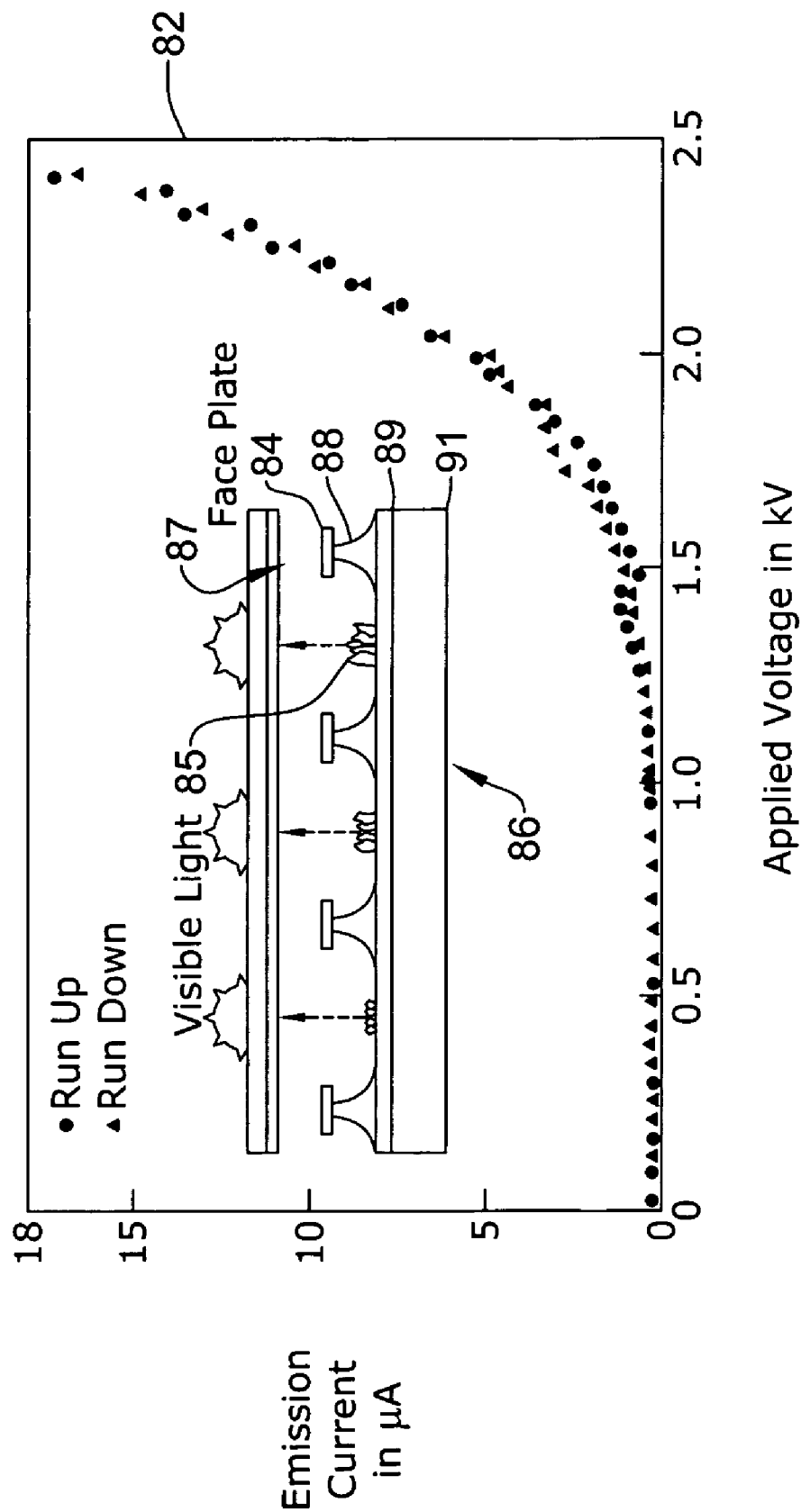
FIG. 11a is a graphical illustration emission current versus applied voltage for cold-cathode emissions from diamond films.
Figure 11B:
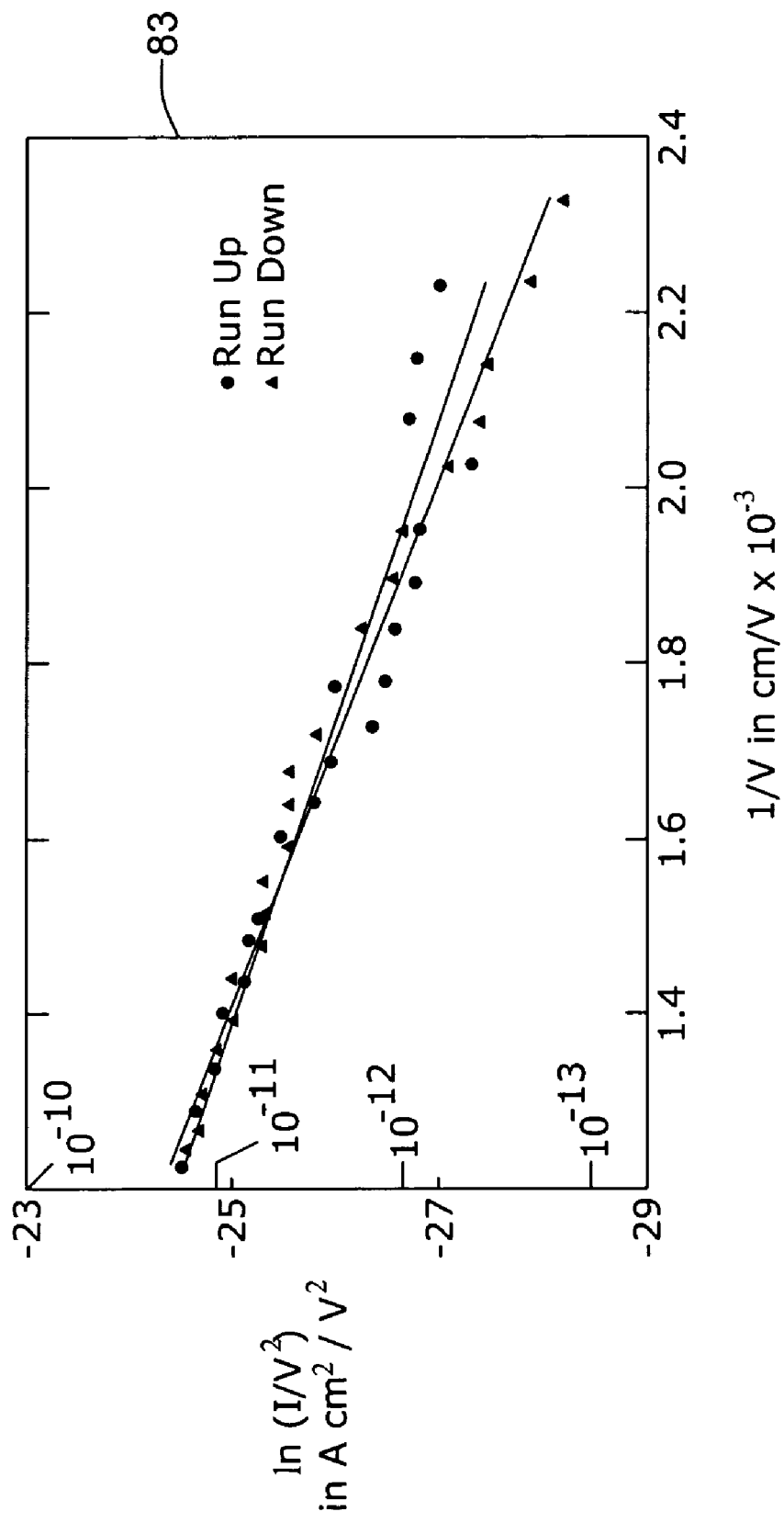
FIG. 11b is restricted Fowler-Nordheim plot of the electron emission of a micro-wave CVD sample.

Cold cathode emission from carbon nanotubes may be used for the electron emitter electrode in the ion pump. The nanotube whiskers may provide for an electrical discharge and operate in a cold cathode field emission mode or a corona discharge mode. FIG. 10 shows a graph 81 about electron cold-cathode emission from a carbon nanotube in terms of current density versus applied voltage. A corona onset may be at 200/0.0063 about 3.1 kV/cm and 600/0.0260 about 2.1 kV/cm. FIG. 11a is a graphical illustration 82 emission current versus applied voltage for cold-cathode emissions from an emitter 85 of a diamond film or the like. The inset is of a device 86 in a display application but may be used for the present ion pump. Such an emission type device may be used as an electron emitter in an MDD of an ion pump. Electrons from emitter 85 may go to a collector 87. The gate 84, situated on an insulator 88, of the emission device 86 in FIG. 11a when used in the present ion pump may be utilized to focus the non-drag action of the pump. Insulator 88 and the diamond emitter 85 may be situated on an electrode 89, which in turn is on a base 91. FIG. 11b shows a restricted Fowler-Nordheim plot 83 of the electron emission of a micro-wave CVD sample.

Although the invention has been described with respect to at least one illustrative embodiment, many variations and modifications will become apparent to those skilled in the art upon reading the present specification. It is therefore the intention that the appended claims be interpreted as broadly as possible in view of the prior art to include all such variations and modifications.

What is claimed is:

1. An ion pump comprising:
an insulating layer;
a first conductive layer situated on the upstream side of the insulating layer;
a second conductive layer situated on the downstream side of the insulating layer;
a plurality of openings situated in the first conductive layer, the insulating layer and the second conductive layer forming channels having a first upstream and a second downstream discharge device electrode, wherein the first electrode has a sharp-like shape at an upstream end and a blunt downstream end, wherein the plurality of openings are grouped into upstream inputs formed by the first electrode and downstream outputs formed by the second electrode, and the openings situated at inputs are formed by upstream sharp-like conductor ends and the openings situated at outputs are formed by downstream non-sharp-like conductor ends; and
an enclosure containing the channels and having an input port proximate to an input side of the plurality of openings and an output port proximate to an output side of the plurality of openings, wherein a fluid in the enclosure can be transported between the input port and output port by being forced through the plurality of openings;
wherein each opening of the plurality of openings is sized for a ratio, R, of an axial length equal to a thickness of the insulator, to an inner diameter, of each opening to maximize a performance of the pump, having approximately $1 \leq R \leq 10$, and the thickness of the insulator about 6 µm $\leq S \leq$ 100 µm.

2. An ion pump comprising:
an insulating layer;
a first conductive layer situated on the upstream side of the insulating layer;
a second conductive layer situated on the downstream side of the insulating layer;
a plurality of openings situated in the first conductive layer, the insulating layer and the second conductive layer forming channels having a first upstream and a second downstream discharge device electrodes, wherein the first electrode has a sharp-like shape at an upstream end and a blunt downstream end, wherein the plurality of openings are grouped into upstream inputs formed by the first electrode and downstream outputs formed by the second electrode, and the openings situated at inputs are formed by upstream sharp-like conductor ends and the openings situated at outputs are formed by downstream non-sharp-like conductor ends;
an enclosure containing the channels and having an input port proximate to an input side of the plurality of openings and an output port proximate to an output side of the plurality of openings, wherein a fluid in the enclosure can be transported between the input port and output port by being forced through the plurality of openings; and
a number of consecutive stages, L, of channels, and having an applied voltage, U, as required to achieve a desired total pressure head, $\Delta p_t = n \cdot \Delta p$, where an achieved pressure head at each stage is about Δp, including compensation for the changes in absolute pressure, gas volume due to compressibility, and temperature at each stage, which entails changes in pump effectiveness and capacity at each stage;
wherein a number of openings, n, of the plurality of openings, stages, L, and applied voltage, U, are selected so that a desired total pumping volumetric rate and total pump head pressure can be achieved, including compensation for a pressure drop through the pump, and a required number of openings, $n_o$, and compensation for a pressure drop through the analyzer load; and
wherein:
the number of openings, n, is increased by a factor $\alpha = n/n_o = \Delta p_o/(\Delta p_o - \Delta p_L)$;
$\Delta p_o$ = pump pressure head without a load;
$\Delta p_L$ = pressure drop through the load; and
$\Delta p_o \sim 2 \cdot \Delta p_L$.

3. An ion pump comprising:
an insulating layer;
a first conductive layer situated on the upstream side of the insulating layer;

a second conductive layer situated on the downstream side of the insulating layer;

a plurality of openings situated in the first conductive layer, the insulating layer and the second conductive layer forming channels having a first upstream and a second downstream discharge device electrodes, wherein the first electrode has a sharp-like shape at an upstream end and a blunt downstream end, wherein the plurality of openings are grouped into upstream inputs formed by the first electrode and downstream outputs formed by the second electrode, and the openings situated at inputs are formed by upstream sharp-like conductor ends and the openings situated at outputs are formed by downstream non-sharp-like conductor ends; and an enclosure containing the channels and having an input port proximate to an input side of the plurality of openings and an output Port proximate to an output side of the plurality of openings, wherein a fluid in the enclosure can be transported between the input port and output port by being forced through the plurality of openings;

wherein the sharp-like conductor ends and non-sharp-like conductor ends are situated in the first conductive layer to generate in-situ ions proximate to the sharp-like conductor ends;

the in-situ ions predominantly have the polarity of the sharp-like conductor ends, which then induce a fluid flow of neutral molecules as a result of a force and viscous drag of the in-situ ions and away from the sharp-like conductor ends; and wherein each of the sharp-like conductor ends are recessed to a larger inner diameter than an inner diameter of each of the plurality of openings in the insulating layer, by a distance equal to about 10 to 20 percent of the inner diameter of an opening in the insulating layer, to enable removal of non-predominant polarity ions before remaining predominant ions enter the inside diameters of the plurality of openings in the insulating layer.

\* \* \* \* \*